(12) United States Patent
Stroebech et al.

(10) Patent No.: US 11,389,108 B2
(45) Date of Patent: Jul. 19, 2022

(54) METHOD AND DEVICE FOR CAPTURING AND DIGITALLY STORING IMAGES OF A WOUND, FISTULA OR STOMA SITE

(71) Applicant: Coloplast A/S, Humlebaek (DK)

(72) Inventors: Esben Stroebech, Hoersholm (DK); Pernille Troejgaard, Humlebaek (DK); Bjoern Jan Fiksak, Gilleleje (DK)

(73) Assignee: Coloplast A/S, Humlebaek (DK)

( * ) Notice: Subject to any disclaimer, the term of this patent is extended or adjusted under 35 U.S.C. 154(b) by 1185 days.

(21) Appl. No.: 15/311,194

(22) PCT Filed: May 15, 2015

(86) PCT No.: PCT/EP2015/060767
§ 371 (c)(1),
(2) Date: Nov. 15, 2016

(87) PCT Pub. No.: WO2015/173395
PCT Pub. Date: Nov. 19, 2015

(65) Prior Publication Data
US 2017/0079576 A1   Mar. 23, 2017

(30) Foreign Application Priority Data

May 15, 2014   (DK) .......................... PA 2014 70286

(51) Int. Cl.
*A61B 5/00* (2006.01)
*A61F 5/445* (2006.01)

(52) U.S. Cl.
CPC ............ *A61B 5/445* (2013.01); *A61B 5/0079* (2013.01); *A61B 5/4851* (2013.01); *A61B 5/742* (2013.01);
(Continued)

(58) Field of Classification Search
None
See application file for complete search history.

(56) References Cited

U.S. PATENT DOCUMENTS 6,171,289 B1 * 1/2001 Millot ..................... A61F 5/443
604/336
7,448,753 B1   11/2008 Chinnock
(Continued)

FOREIGN PATENT DOCUMENTS

CN           1836240         9/2006
CN        101431607 A        5/2009
(Continued)

OTHER PUBLICATIONS

Yeo et al., Management of parastomal ulcers, World J. Gastoenterol, May 28, 2006, pp. 3133-3137. (Year: 2006).*

*Primary Examiner* — Katherine L Fernandez
(74) *Attorney, Agent, or Firm* — Coloplast Corp., Coloplast A/S; Nick Baumann (57) ABSTRACT

In a method and handheld device for capturing and digitally storing images of a wound, stoma, fistula or stoma wafer site, a representation of a view field of an optical lens of a camera is represented at a monitor. A marker is inserted in the representation of the view field in the monitor before an image is stored, the marker being configured to aid a user's positioning of the digital camera relative to the wound area, stoma, fistula or wafer. The patient holds the handheld wound and stoma imaging device in a position relative to his/her own body or in relation to the wafer, while the monitor is simultaneously viewable by the patient. Upon receipt of auser-input for effecting digital storage of the image in the view field, the image is stored in a memory of the handheld wound and stoma imaging device. The device may include a tablet device of smart phone suitably programmed by means of an applet, and optionally an adapter for facilitating the patient's handling of the device.

12 Claims, 12 Drawing Sheets

(52) U.S. Cl.
CPC ............ *A61B 5/7485* (2013.01); *A61F 5/445* (2013.01); *A61B 2560/0431* (2013.01); *A61B 2560/0475* (2013.01); *A61B 2576/00* (2013.01)

(56) References Cited

U.S. PATENT DOCUMENTS

| | | | |
|---|---|---|---|
| 8,634,657 | B2 | 1/2014 | Sakamoto |
| 8,692,900 | B2 | 4/2014 | Denisenkov et al. |
| 2003/0189647 | A1 | 10/2003 | Kang |
| 2005/0001908 | A1 | 1/2005 | Lee |
| 2005/0276596 | A1 | 12/2005 | Chan et al. |
| 2007/0276309 | A1 | 11/2007 | Xu et al. |
| 2008/0049134 | A1* | 2/2008 | Saito ................ G02B 7/023 348/333.02 |
| 2009/0284378 | A1* | 11/2009 | Ferren ............... G08B 21/06 340/573.1 |
| 2010/0225784 | A1 | 9/2010 | Sato et al. |
| 2011/0164147 | A1 | 7/2011 | Takahashi et al. |
| 2012/0143617 | A1 | 6/2012 | Connors et al. |
| 2012/0194702 | A1 | 8/2012 | Naka |
| 2012/0253224 | A1 | 10/2012 | Mir et al. |
| 2013/0028586 | A1 | 1/2013 | Ide et al. |
| 2013/0057713 | A1 | 3/2013 | Khawand |
| 2013/0058619 | A1 | 3/2013 | Miyakawa et al. |
| 2013/0114938 | A1 | 5/2013 | Kuriyama |
| 2013/0135871 | A1 | 5/2013 | Harooni |
| 2013/0335545 | A1* | 12/2013 | Darling ............... A61B 5/742 348/77 |
| 2014/0088402 | A1* | 3/2014 | Xu ..................... A61B 5/6898 600/407 |
| 2014/0236111 | A1* | 8/2014 | Casado ................ A61F 5/445 604/332 |
| 2016/0058673 | A1* | 3/2016 | Francis ............... G16H 20/17 604/65 |
| 2017/0000407 | A1* | 1/2017 | Saxby ............... A61B 5/4848 |
| 2017/0124709 | A1* | 5/2017 | Rithe ................ G06K 9/2036 |

FOREIGN PATENT DOCUMENTS

| | | |
|---|---|---|
| CN | 201936237 U | 8/2011 |
| CN | 102339092 A | 2/2012 |
| JP | 10313422 A2 | 11/1998 |
| JP | 2007318773 A2 | 12/2007 |
| JP | 2013070116 A2 | 4/2013 |
| JP | 2013165318 A2 | 8/2013 |
| KR | 20100103083 A | 9/2010 |
| KR | 20130103960 A | 9/2013 |
| RU | 52563 U1 | 4/2006 |
| WO | 2005017806 | 2/2005 |
| WO | 2007133555 A2 | 11/2007 |
| WO | 11087807 A2 | 7/2011 |
| WO | 13096766 A2 | 6/2013 |
| WO | 2014045558 A1 | 3/2014 |

* cited by examiner

METHOD AND DEVICE FOR CAPTURING AND DIGITALLY STORING IMAGES OF A WOUND, FISTULA OR STOMA SITE

TECHNICAL FIELD

The present invention relates to a method and a handheld device for capturing and digitally storing images of a site selected among a wound area at a body of a patient, a skin area surrounding a stoma projecting from a body portion of a patient, and a worn wafer of an ostomy system. Further, the invention relates to an adapter for use with the handheld device. The invention is particular useful for aiding patients' imaging of their own wound, stoma or worn wafer.

BACKGROUND OF THE INVENTION

Ostomy systems typically comprise a wafer, also referred to as a base plate, comprising an adhesive area surrounding an opening for accommodating the patient's stoma.

Ostomy systems may include a one-piece or a two-piece system. Both kinds include an adhesive wafer and a collection pouch. The pouch attaches to the abdomen by the adhesive wafer and is fitted over and around the stoma to collect body waste. The wafer and its adhesive are designed to protect the skin from the stoma output and to be as skin-friendly as possible. Two-piece systems allow pouches to be changed while leaving the wafer attached to the skin, whereas in one-piece systems the pouch and wafer come as a single integrated unit, which is to be replaced in its entirety when the pouch is changed.

Wound dressings typically comprise an absorbent material for making contact with the wound and covered on its opposite side by a pliant protective sheet or film. A flange surrounding the absorbent material and having an adhesive side facing the body of the patient is normally provided for attaching the dressing to healthy skin surrounding the wound.

Ostomy and wound dressings have developed considerably over the past decades as a result of research and development relating, inter alia, to skin-friendly and nearly leakage-proof adhesives, customizable wafers of ostomy systems, pliant materials and structures, absorbents, etc. Yet, performance and user-customization may suffer as a result of product defects, incorrect use of products, poor wound healing, etc. In order to be able to continuously improve the quality of life of wound and ostomy patients, states of wound healing, leakage of wound or ostomy systems, and skin irritation are frequently monitored, not only by patients themselves, but also by physicians and suppliers of wound and ostomy systems. In order for such monitoring to successfully result in improvements, patients' and physicians' examination of worn ostomy wafers or wound or ostomy sites need to be reliable and as objective as possible. Examination of wound or ostomy sites of worn ostomy wafers is often impeded by the costs and inconveniences associated with bringing patients or their worn ostomy wafers together with physicians or other adequately educated personnel.

Attempts to provide methods and systems relying on image capturing of sites of interest have only enjoyed limited success for various reasons. Firstly, experience shows that patients' attempts to capture images of their own stoma or wound sites often fail due to difficulties in positioning cameras correctly in relation to their bodies. Even if images are captured, they may often be out of focus, or they may not capture the area of interest, which is to be examined. Secondly, dedicated camera positioning equipment developed so far has been found to be bulky, expensive and inconvenient in use. Thirdly, due to the aforementioned drawbacks and further due to difficulties in transmitting images to adequately educated personnel, patients may easily tend to forget or give up image capturing.

Embodiments of the present invention aim at improving the quality of examination of wound sites, ostomy sites and/or worn ostomy wafers, as well as at facilitating such examination. It is one object of embodiments of the present invention to enable qualified examination of wound or ostomy sites and/or worn ostomy wafers to be carried out without bringing patients or their worn ostomy wafers together with physicians or other personnel. It is a further object of embodiments of the invention to facilitate patients' own capturing of high-quality images of their wound or stoma sites or worn wafers. It is a further object of embodiments of the invention to provide measures allowing for reliable examination of wound, ostomy and wafer sites on the basis of photographic images of such sites.

SUMMARY OF THE INVENTION

In a first aspect, the invention provides a method for capturing and digitally storing images of a site selected among:
 a wound area at a body portion of a patient,
 a skin area surrounding a stoma projecting from a body portion of a patient,
 a fistula area at a patient's skin and
 an adhesive area of worn wafer of an ostomy system;
 the method comprising:
 providing a handheld wound and stoma imaging device comprising at least one digital camera having an optical lens and a monitor operatively connected to or integrated with the camera;
 displaying a representation of an image within a view field of the optical lens at the monitor;
 inserting a marker in the representation of said view field in the monitor before an image is stored, said marker being configured to aid a user's positioning of the digital camera relative to the wound area, stoma, fistula or wafer in order to capture the wound area, the skin area surrounding the stoma or fistula, or an area of interest of the wafer;
 the patient holding the handheld wound and stoma imaging device in a position relative to his/her own body or in relation to the wafer, in which the wound, stoma, fistula or wafer is within the view field of the optical lens, while the monitor is simultaneously viewable by the patient;
 receiving, at the handheld wound and stoma imaging device, a user-input for effecting digital storage of the image in said view field;
 storing the image in a non-volatile memory of the handheld wound and stoma imaging device.

In a second aspect, the invention provides a handheld wound and stoma imaging device for capturing and digitally storing images of a site selected among:
 a wound area at a body portion of a patient,
 a skin area surrounding a stoma projecting from a body portion of a patient,
 a fistula at a patient's skin, and
 a worn wafer of an ostomy system;
 the device comprising:
 at least one digital camera comprising an optical lens;

a monitor operatively connected to or integrated with the camera and configured to display a representation of an image within a view field of the optical lens;

a controller for inserting a marker in the representation of said view field at the monitor before an image is stored by activation of the input device, said marker being configured to aid a user's positioning of the digital camera relative to the wound, stoma, fistula or wafer in order to capture the wound area or the skin area surrounding the stoma, fistula or an area of interest of the wafer;

an input device for receiving a user-input for effecting digital storage of the image in said view field upon user-activation of the input device;

a non-volatile memory for storing said image.

In a third aspect, the invention provides an adapter for a handheld device according to the second aspect of the invention, comprising:

a wall structure for supporting a portable unit comprising a camera and a monitor;

a fixation structure for releasably securing the portable unit to the wall structure, wherein wherein at least a portion of a back face of the wall structure is permanently inclined or tiltable relative to a front face of the wall structure.

It will be appreciated that the present invention relies on digital images of wound, ostomy and/or wafer sites of interest for examination thereof. In particular, the provision of a marker in the view field in the monitor, the user's positioning of the camera relative to the wound area, stoma or wafer is facilitated. The user, notably the patient, is hence aided in positioning the camera at a distance and an angle relative to the wound, stoma or wafer area of interest, which results in the recording of an image of sufficient quality for subsequent examination thereof.

It should be understood that the marker referred to herein is digitally generated by a processing unit of the handheld device. The marker may in particular be generated by the processing unit of the handheld device on the basis of digital image processing of the image within the view field of the optical lens at the monitor. Such digital image processing may occur repeatedly in order to update the position of the marker in response to movements of the camera relative to the wound area, stoma, fistula or wafer.

As used herein, the terms 'stoma' and 'ostomy system' relate to uroostomy, ileoostomy and colostomy appliances alike. Stoma-related embodiments of the invention thus relate to systems for urostomies, ileostomies and colostomies.

The handheld device may be programmed and configured to continuously display a preview of the image at the monitor, i.e. to continuously display in the monitor an image representation of the view field of the optical lens. In order to assist the user's positioning of the handheld device relative to the wound or stoma site or worn ostomy system, the handheld device may be configured to continuously process the representation of the view field and to identify an area of interest therein. For example, an area of interest may include the patient's stoma or wound area, which may be identifiable on the basis digital image processing to identify areas with a high proportion of particular colour, typically red. The handheld device may thus be further configured to aid the patient's positioning of the handheld device and thus of the camera by, for example, insertion of said marker in the monitor at the area of interest. Thus, in the image representation in the monitor, the marker may be movable, whereby the variable position of the marker may be controllable on the basis of the aforementioned processing which continuously identifies an area of interest. Alternatively or additionally, the handheld device may provide audio or video instructions to the user via the monitor and/or a loudspeaker of the handheld device assisting the patient's positioning of the camera.

The stored image of the wound, stoma or wafer area of interest may be digitally processed or examined within the handheld wound and stoma imaging device. Alternatively, the handheld device may comprise a data communication interface for transmitting the digital image to an external device for processing thereof. Digital processing of the image may be complemented by inspection by a human being where necessary or desired. The digital, i.e. computerized processing of the image may provide a measure of a state of healing and/or irritation of the wound or skin and/or a measure of a degree of leakage of the wafer and/or a qualitative state of an adhesive at the wafer. In particular, the method and device of the present invention may assess the extent and severity of skin change, including peristomal skin change, in terms of discolouration (D), erosion (E), and tissue overgrowth (T) in accordance with the DET score scheme known per se. The DET score or other measure of skin change and/or state of healing and/or state of the adhesive wafer may be supplemented by patient-input, such as input received through a user interface of the handheld device, e.g. in the form of answers to a questionnaire.

In one embodiment, the digitally processed image may be used for monitoring a post-operational state of healing of a new stoma.

During processing of the image, one or more predetermined positions may be located within the image, at which colour changes, colours, contrasts, surface texture or patterns or other structures may be recognized by image analysis procedures. For example, measures of colour changes, colours, contrasts, surface textures or patterns or other structures may be compared to predetermined or prestored reference values for the selected positions.

In the handheld device according to the present invention, the camera, monitor and controller are preferably integrated in a single portable unit. Preferably, the integrated portable unit also comprises software for image analysis and/or for transmission of captured images to an external device. For example, the handheld device may be embodied as a suitably programmed general purpose smart phone or tablet device. The software required for inserting the marker in the view field and for performing other optional operations, such as instructing the user, processing and assessing digital images and/or presenting questionnaires to the user may be loaded into the device as an applet.

For the purpose of facilitating the user's, notably the patient's handling of the device, an adapter may be provided with the device as an integrated part thereof or as a separate detachable structure. In one embodiment, the adapter may comprise a wall structure for supporting the portable unit, and a fixation structure at an interior portion of the wall structure for releasably securing the portable unit to the adapter. The adapter may be configured to allow the monitor of the portable unit to be viewed by a patient holding the adapter with the portable unit mounted therein in a position relative to the patient's own wound or stoma while the patient captures an image of the wound or stoma area. Further, the adapter may be configured to expose the input device so that it is accessible to the patient for effecting capturing and digitally storing of the image of the patient's own wound or stoma. Certain embodiments of the adapter may be tailored for stoma imaging, whereas other embodiments of the adapter may be tailored for wound imaging or for wafer imaging.

When the adapter is mounted to the portable unit integrating the camera, monitor and controller, the monitor may define a front face of the device, and the wall structure may define a back face of the device. For wound and stoma imaging purposes, the back face may define an acute angle with respect to the front face in order for the front face including the optical lens of the camera to lie essentially parallel to a region of interest at the patient's body, such as the patient's abdominal region, while the back face provides a convenient and ergonomic grip for the user's hands. An outer portion of the wall structure may thus define a handgrip structure shaped and sized to fit a hand or two hands of a human being.

In one embodiment, the optical lens of the camera of the handheld device is provided on the back face of the device, i.e. on that face of the device, which is opposite to the monitor. In another embodiment of the invention, the optical lens of the camera is provided on the front face of the device, i.e. on that face of the device, which accommodates the monitor. The hand-grip portion of the housing or wall structure of the adapter may be collapsible to allow the adapter to more conveniently fit into a bag or pocket.

Embodiments are envisaged, in which the at least one camera comprises a plurality of cameras, notably at least two cameras, one of which is provided at the front face of the device, and another one of which is provided at the back face of the device. The camera at the front face of the device, referred to herein as the front camera, is preferably used for capturing images of wound and stoma sites at patients' bodies. The camera at the back of the device, referred to herein as the back camera, is preferably used for capturing images of worn ostomy wafers or worn wound dressings.

At least a portion of the back face of the wall structure of the adapter or the entire back face may be permanently inclined or titlable relative to the front face of the wall structure. In embodiments, in which a portion of the back face or the entire back face is permanently inclined relative to the front face, the adapter may be provided as a rigid unit, with a hand-grip portion thereof optionally being collapsible or foldable. Embodiments featuring a titable back face may e.g. be provided as wallet-type adapters with mutually hinged flaps, optionally provided with a structure, such as a pair of supports, for keeping the flaps at a desired mutual angle.

The adapter may comprise a mirror arranged to allow the monitor of the portable unit to be viewed from a position, at which the monitor is not directly viewable. Such a configuration may in particular be beneficial for uses, in respect of which the monitor is not visible to the patient when the monitor is held in its intended image-capturing position relative to the patient's body. The provision of the mirror as part of the adapter eliminates the need for a separate mirror or for assistance to the patient by a further person.

Generally, a light source for providing illumination to a skin, wound, stoma or wafer area of interest may be provided with the adapter, preferably as an integrated part thereof.

The marker within the representation of the view field in the monitor may preferably comprise a frame within the image, such as for example a circular or rectangular frame indicating to the user that the wound, stoma or wafer area of interest should be positioned within the frame when the image is captured.

In embodiments, in which the monitor comprises or consists of a touchscreen, capturing of an image may be effected by the patient touching an image-capturing portion of the view field. Alternatively, a separate button may be provided as a hardware element at the handheld device, whereby image capturing may be carried out when the patient presses the button.

The quality of the captured image may be improved in embodiments, in which a plurality of successively captured images is being captured independently from user activation of the input device. For example, the handheld device may comprise an image capturing controller configured to continuously store the plurality of successively captured images. The plurality of successively captured images may be temporarily stored in a first-in-first-out buffered volatile memory of the device, and the image analysis software may be configured to perform a qualitative assessment of the plurality of successively captured images upon user-activation of the input device, and eventually select and store one of the plurality of successively captured images as the image stored in said non-volatile memory. In the present context, the term volatile memory is to understood as a memory which is allowed to be overwritten without user-interaction, whereas the term non-volatile memory is to be understood as memory, which, in a normal state of use, is overwritable only upon user action, such as user-initiated deletion of the image.

In general, at least on image is captured.

BRIEF DESCRIPTION OF THE DRAWINGS

Embodiments of the invention will now be further described with reference to the accompanying drawings, in which.

DETAILED DESCRIPTION OF EMBODIMENTS OF THE INVENTION

FIGS. 1-4 show a first embodiment of a handheld device 100 according to the invention. The device 100 comprises an integrated portable unit 104 comprising a monitor 106 and a camera with an optical lens (not visible in FIG. 1). The camera is embedded in the portable unit 104, with the optical lens lying flush with the front surface defined by the monitor 106. The device 100 further comprises an adapter 108 defining a housing or wall structure, which forms a handgrip portion 110 for the patient 102. A back face 112 of the handgrip portion 110 is inclined relative to the front face defined by the monitor 106 in order for the monitor 106 to extend essentially parallel to the patient's 102 abdominal portion including stoma 103, while the adapter 108 fits ergonomically in the patient's hand.

Figure 1:
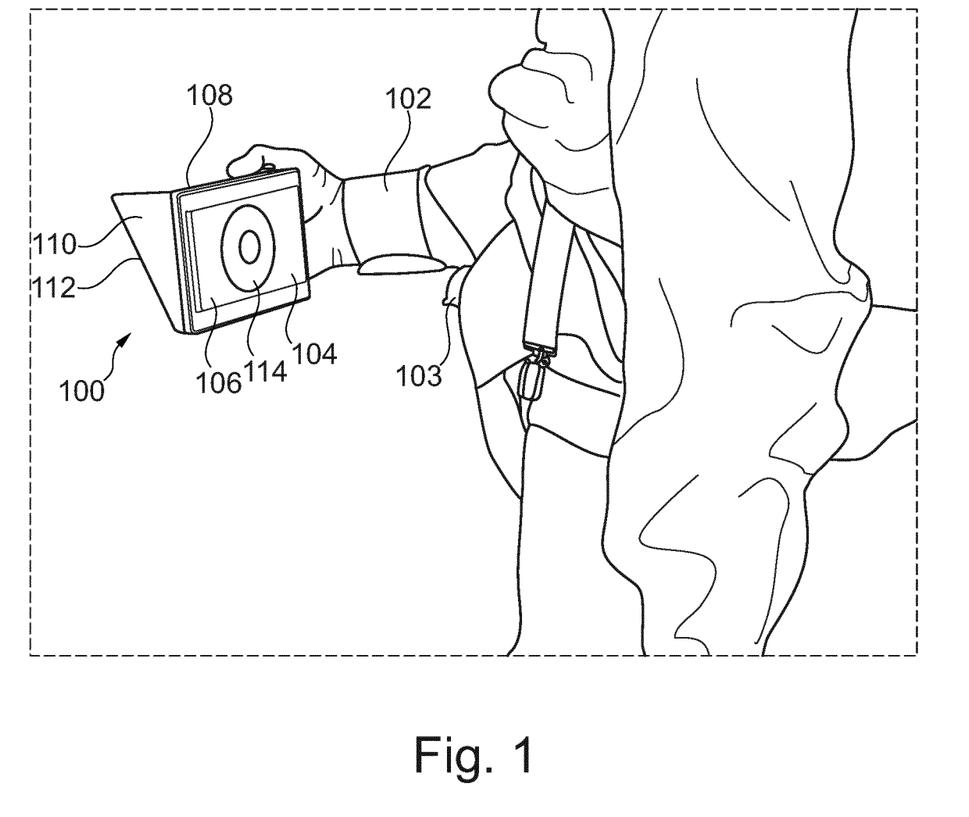
FIGS. 1-4 illustrate a first embodiment of a device according to the invention.
Figure 2:
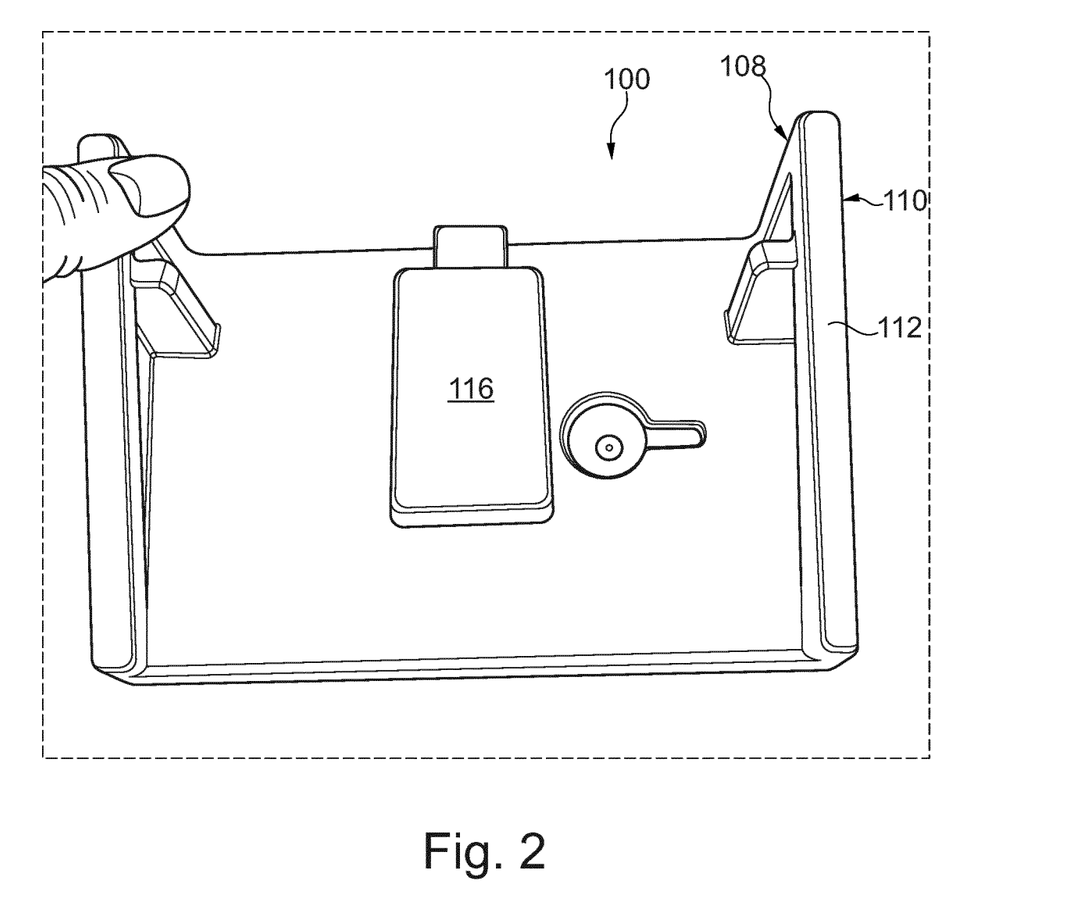
Figure 3:
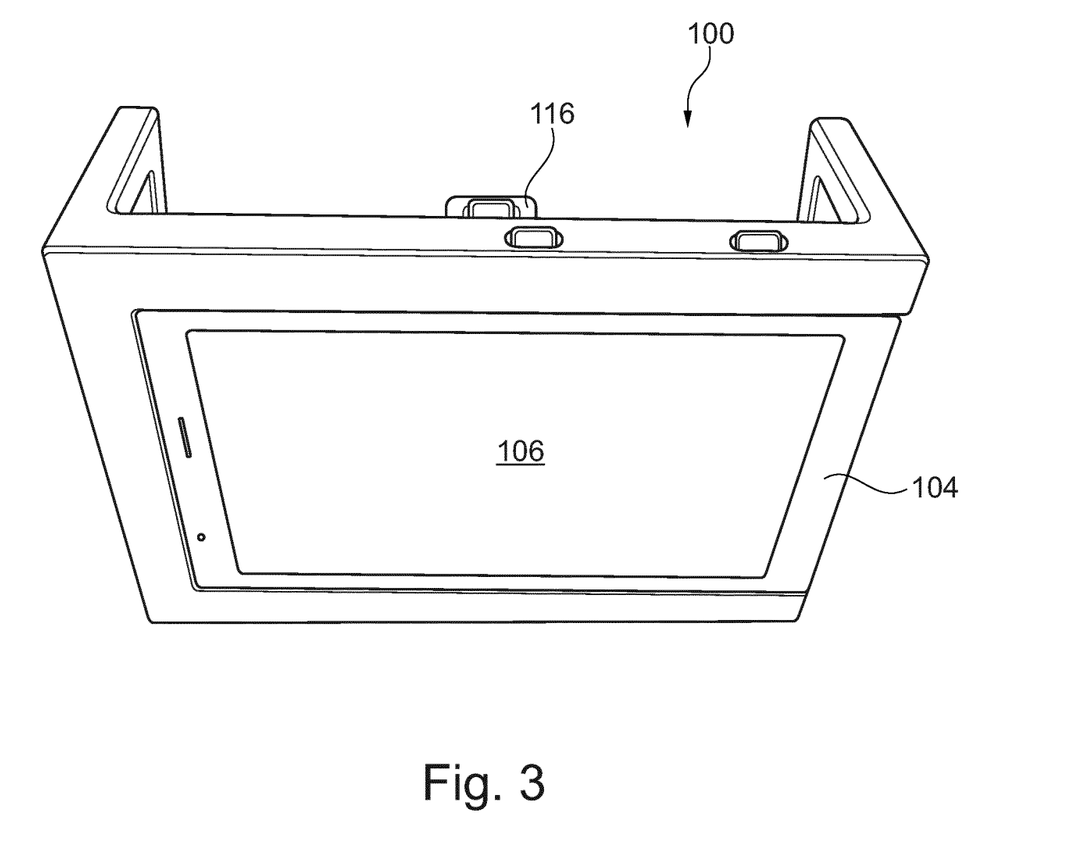
Figure 4:
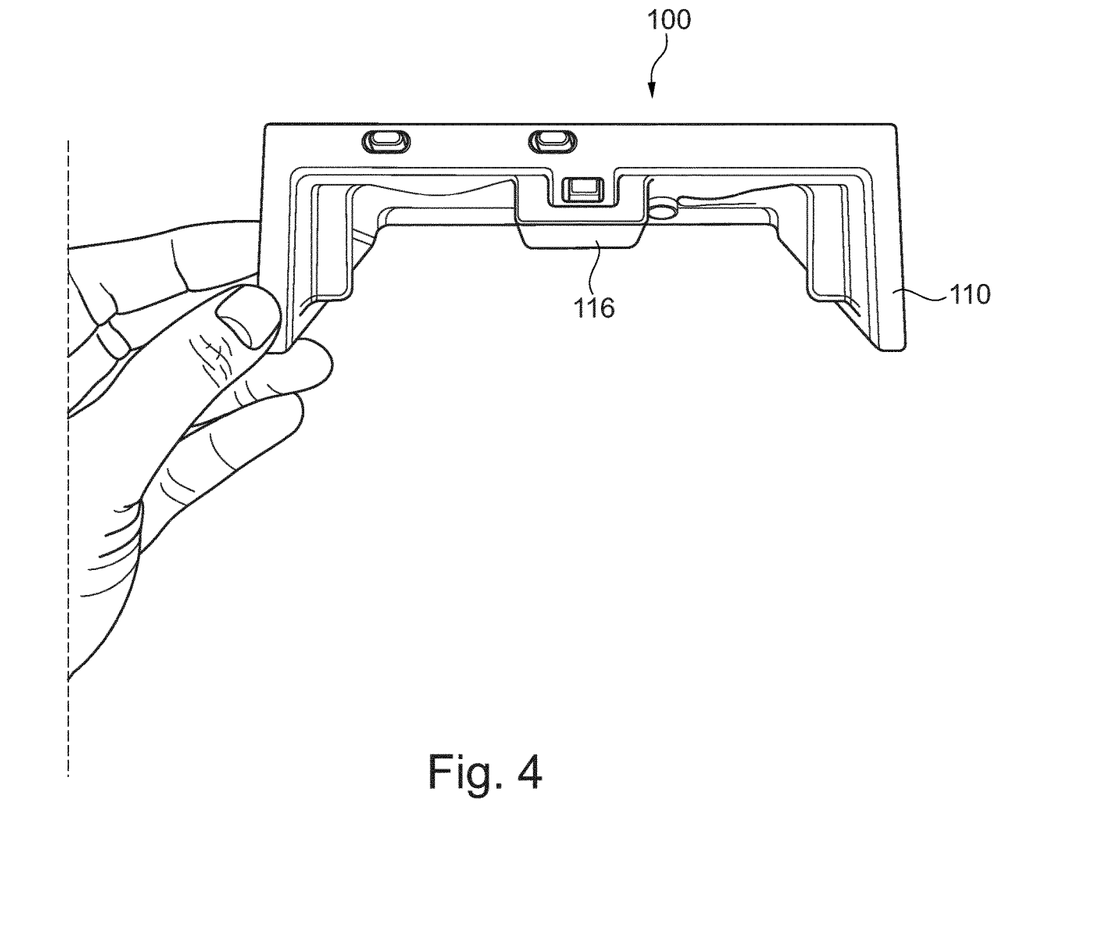
Figure 5:
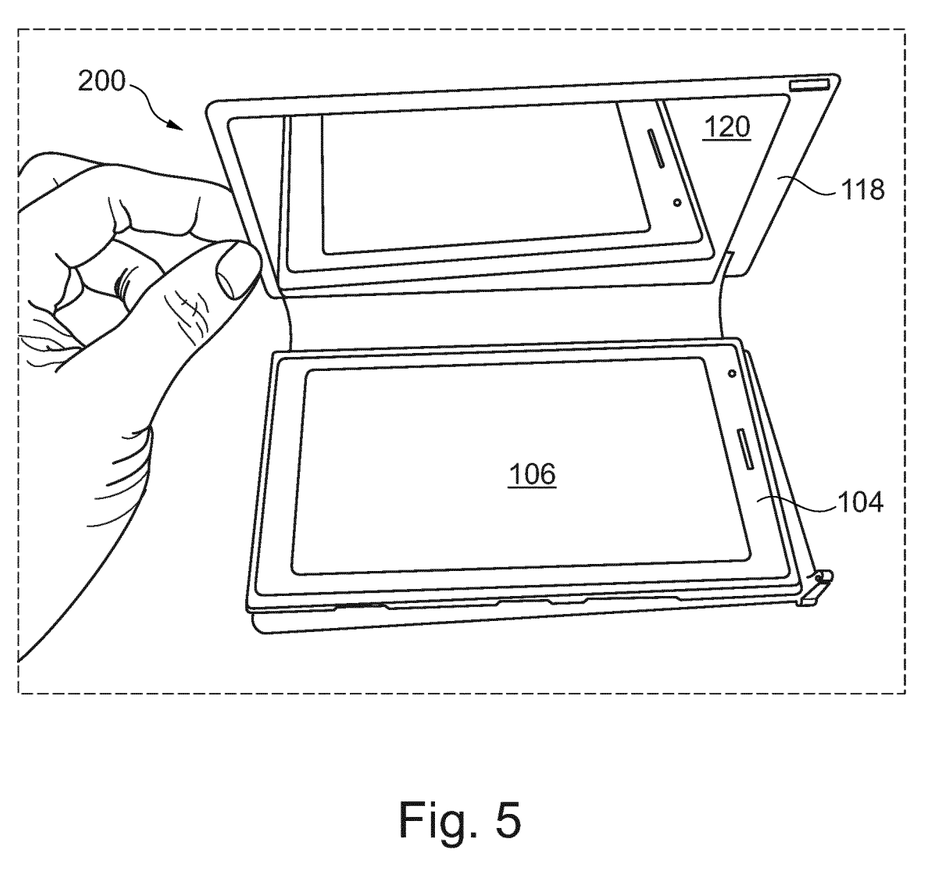
FIGS. 5-8 illustrate a second embodiment of a device according to the invention.

As shown in FIG. 1, a marker 114 is inserted into the view field of the camera represented at the monitor 106. In the embodiment shown, the marker is provided as a circular frame. During use of the device, the patient 102 positions the device 100 such with respect to the stoma 103 or other area to be imaged such that a predetermined area, e.g. the stoma 103 and its peristomal skin, is within the marker 114 in the image representation at the monitor 106. Once the marker 114 and hence the camera is positioned correctly relative to the area of interest to be imaged, the patient may initiate capturing of the image. A plurality of successively captured images may be stored independently from user activation of the device without the user (i.e. patient) being notified thereof. For example, a plurality of successively captured images may be stored in a first-in-first-out buffered volatile memory of the device before or immediately after the user activates the device. Image analysis software of the device may be configured to perform a qualitative assessment of the plurality of successively captured images upon user-activation of the input device, and eventually select and store one of the plurality of successively captured images as the image stored in said non-volatile memory. The user might only notice that a single image has been captured and stored, whereas in fact plural images have been captured. A battery pack 116, such as a rechargeable or replaceable battery pack, is integrated with or releasably mounted to the adapter 118 for powering a light source (not shown).

Figure 6:
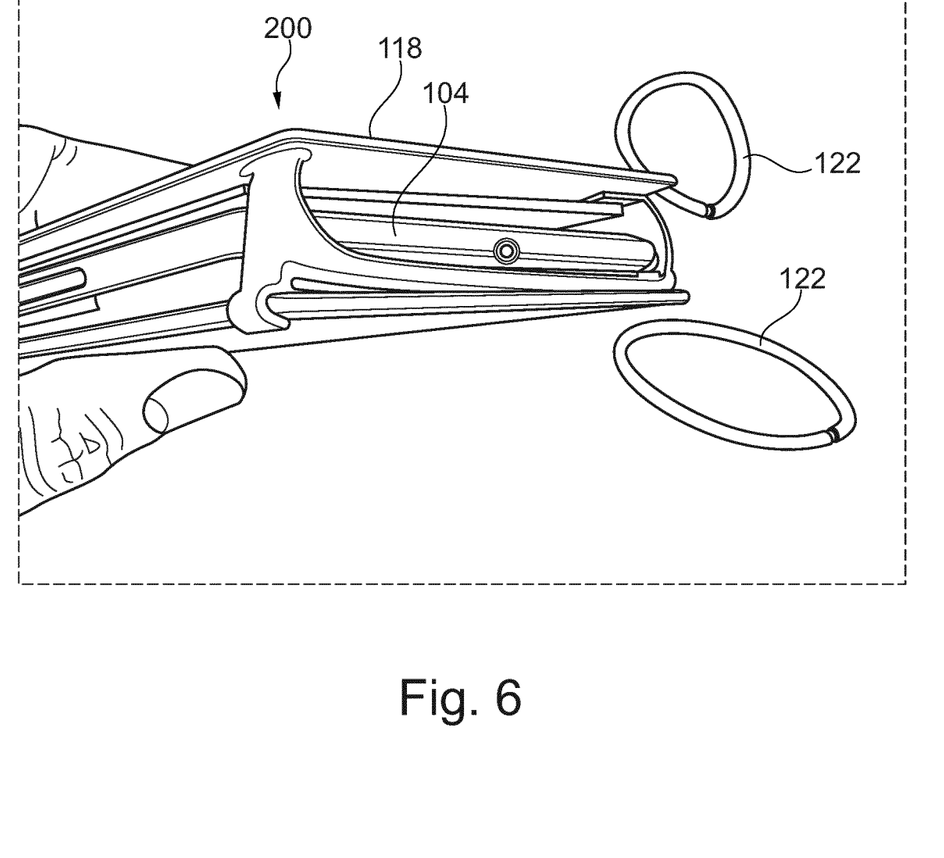
Figure 7:
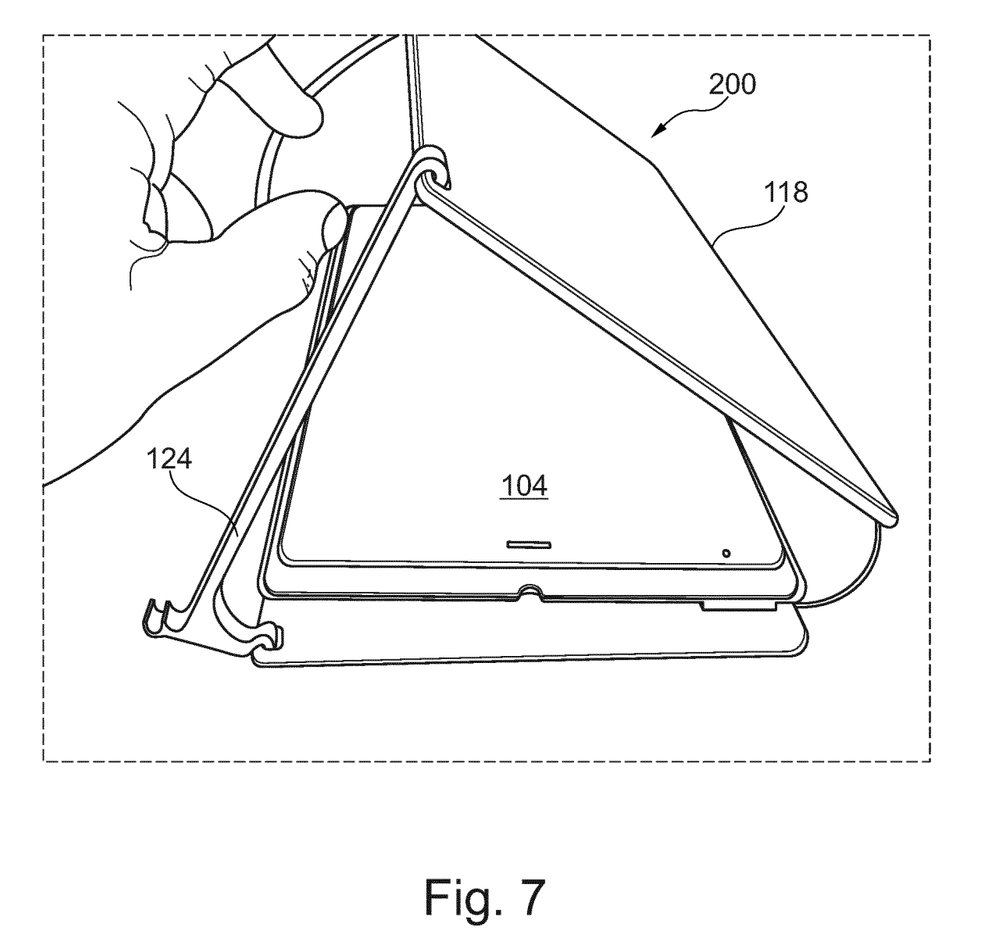
Figure 8:
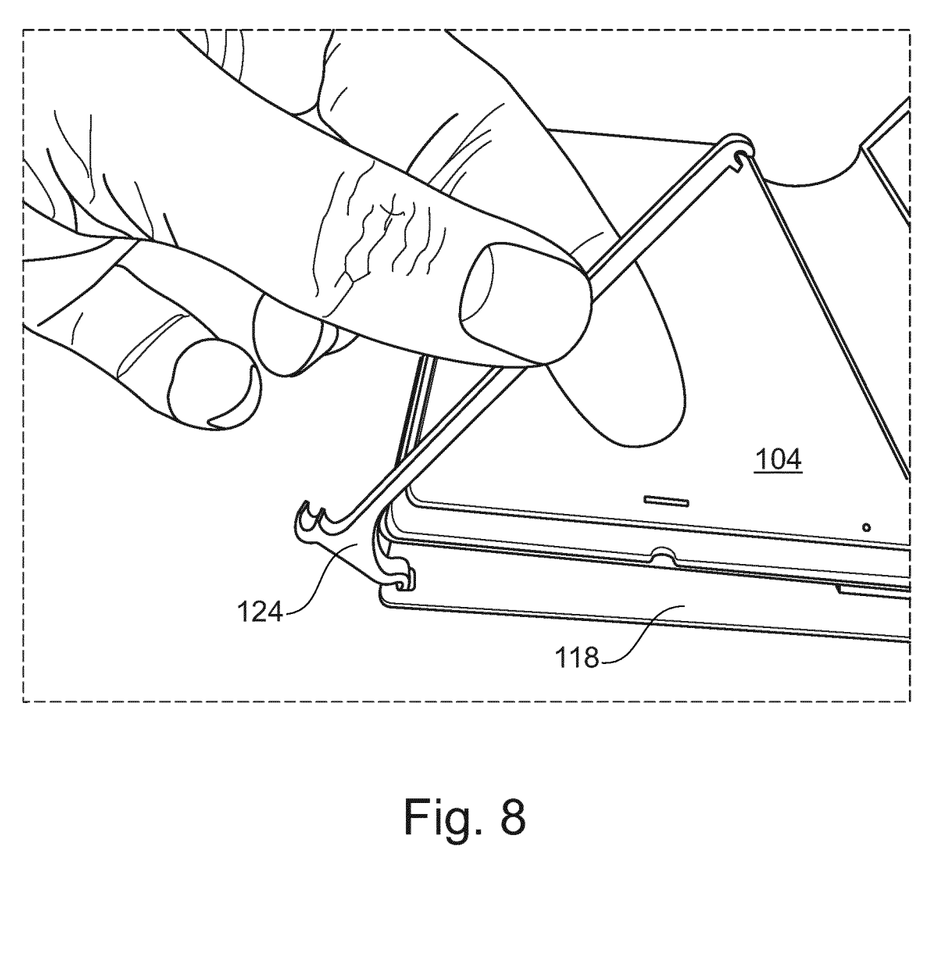

FIGS. 5-8 illustrate a second embodiment of a device 200 according to the invention, which comprises a wallet-type adapter 118 for supporting the integrated portable unit 104. The adapter 188 comprises a mirror 120 for allowing a patient to view a mirrored image of the monitor during uses, in which the monitor 106 is not directly visible to the patient. As shown in FIG. 6, a pair of elastic straps 122 may be provided for keeping the wallet-type adapter 118 in a closed state during non-use conditions. A pair of supports 124 may be provided as shown in FIGS. 7 and 8 for engaging respective flaps of the wallet-type adapter 118, so as to keep the flaps in a desired mutual configuration, notably at a desired mutual angle, during image capturing.

Figure 9:
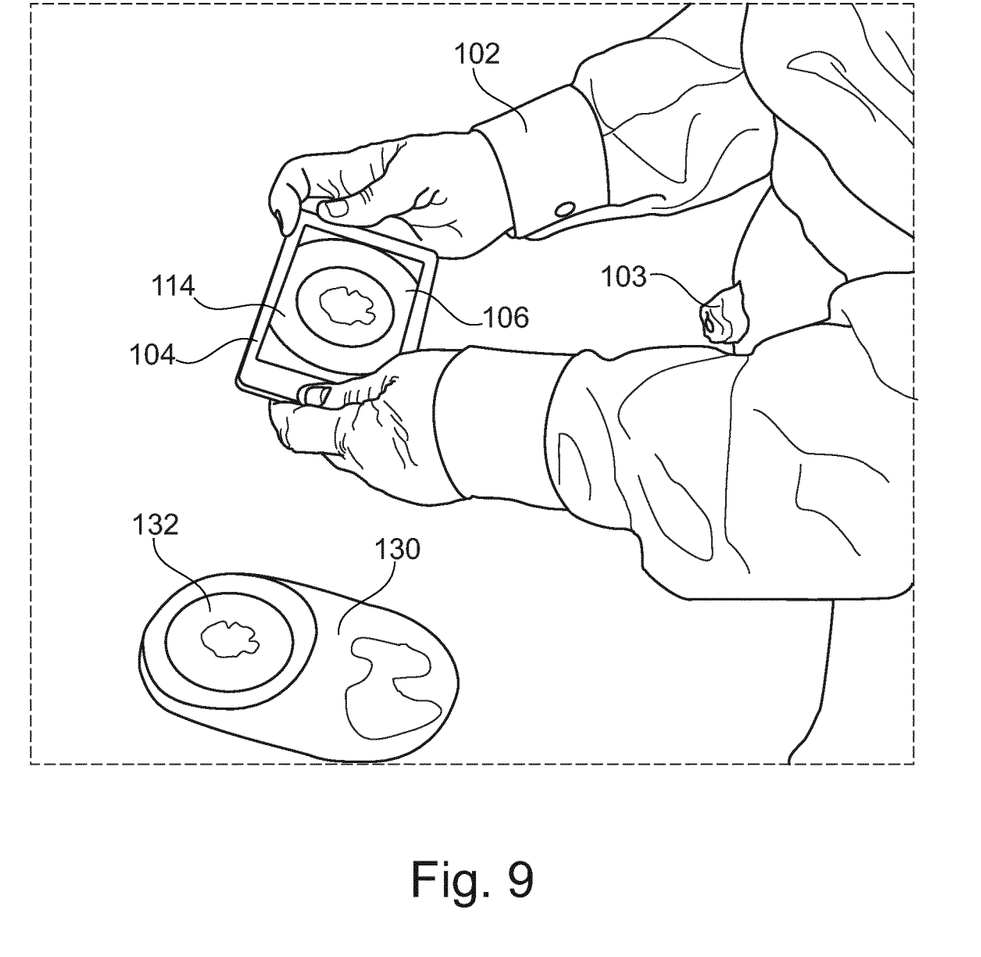
FIG. 9 shows the capturing of an image of an ostomy wafer by means of a device according to the invention.

FIG. 9 shows the capturing of an image of an wafer 132 of an ostomy system 130 by means of a device according to the invention. In FIG. 9, the device is shown with no adapter mounted to the portable unit embedding the camera and monitor 106. The marker 114 aids the patient's positioning of the device 104 relative to the wafer 132.

Figure 10:
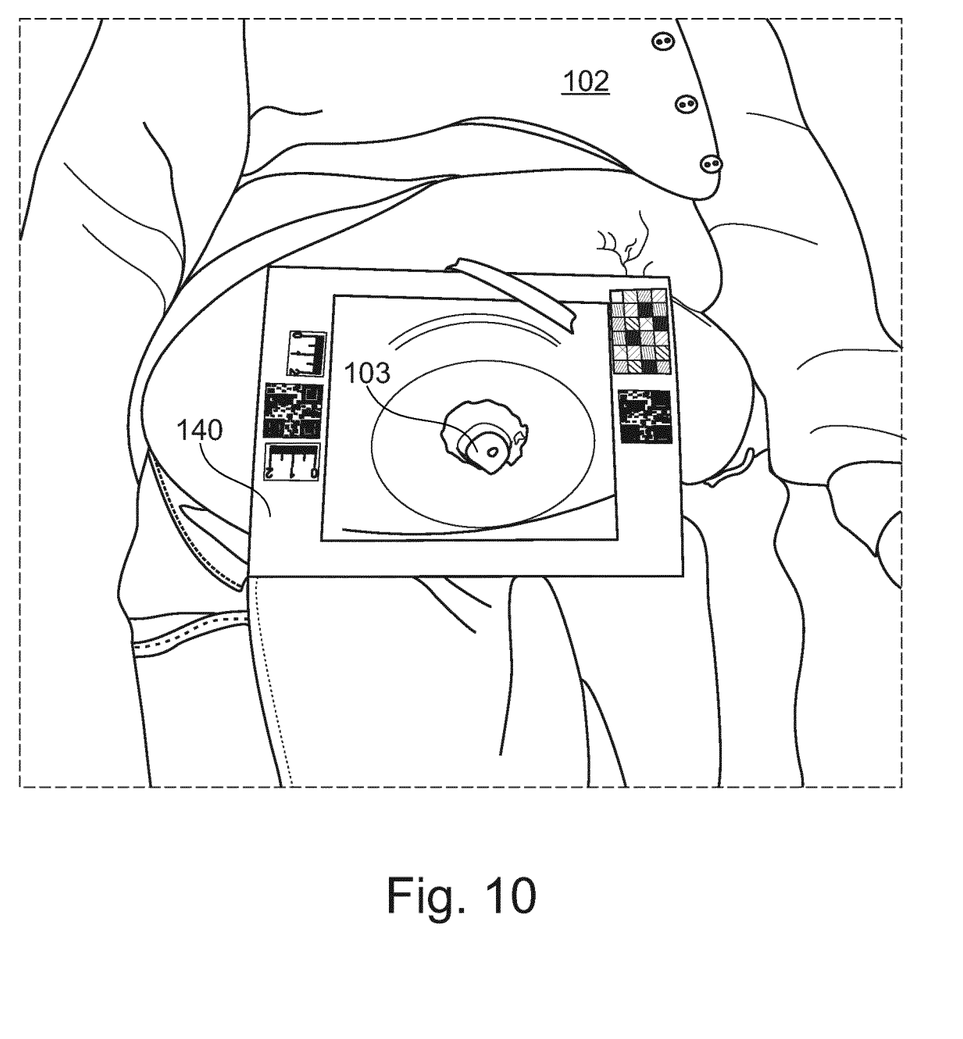
FIGS. 10 and 11 illustrate a colour scale in the vicinity of a stoma of a patient and of an adhesive wafer, respectively, for use as a reference for the camera of the device of the invention.
Figure 11:
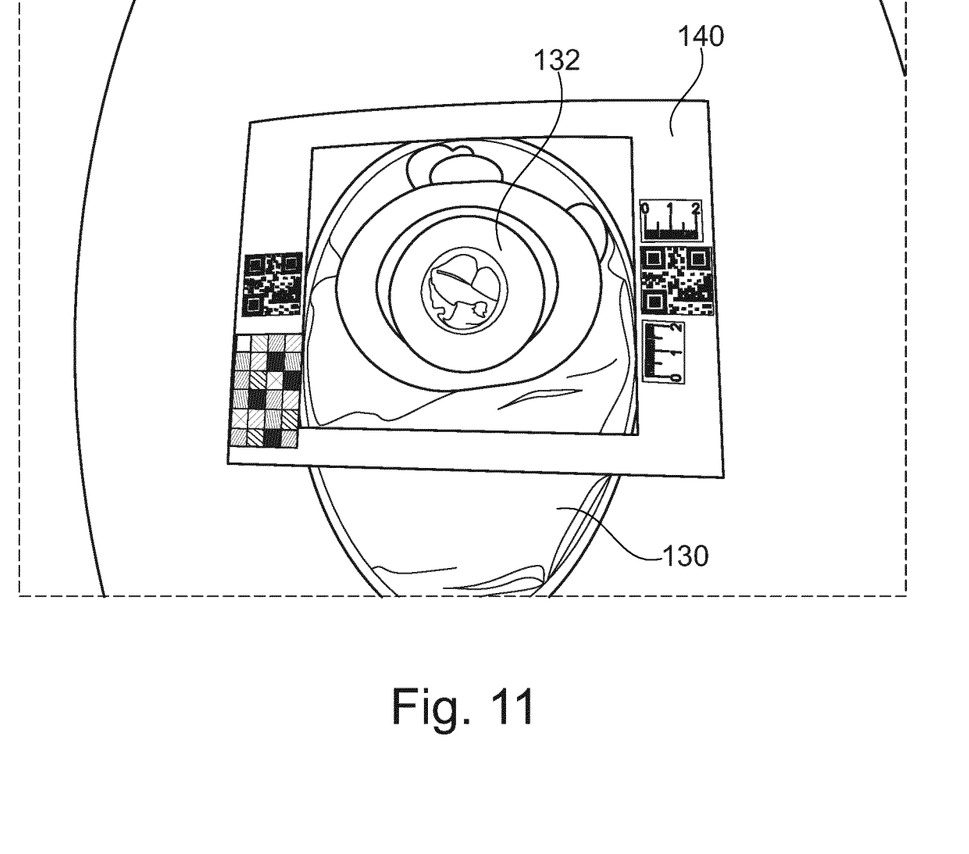

FIGS. 10 and 11 illustrate a colour scale 140 in the vicinity of a stoma 103 of a patient and of an adhesive wafer 132, respectively, for use as a reference for the camera of the device of the invention.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

Figure 12:
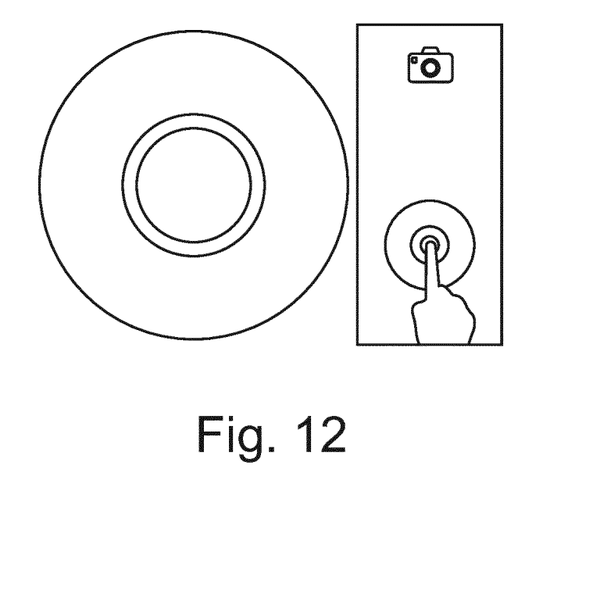
FIGS. 12 and 13 are illustrations of a layout of the monitor of the handheld device when imaging a stoma and a wafer of an ostomy system, respectively.
Figure 13:
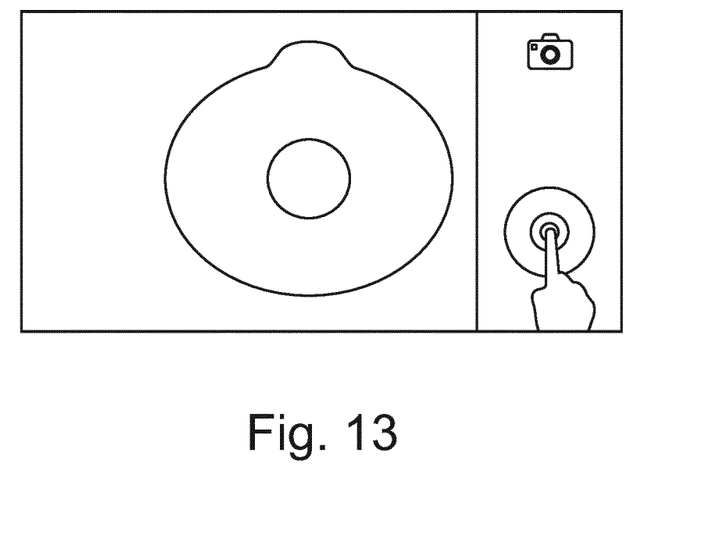

FIGS. 12 illustrates a layout of the monitor of the handheld device when imaging a stoma at a patient's body, and FIG. 13 illustrates a layout of the monitor of the handheld device when imaging a stoma and a wafer of an ostomy system.

The invention claimed is:

1. A method for capturing and digitally storing images of one of a wound area at a body portion of a patient, a skin area surrounding a stoma projecting from the body portion of the patient, and a fistula area in skin of the patient, the method comprising:
providing a handheld wound and stoma imaging device comprising a digital camera having an optical lens and a monitor operatively connected to or integrated with the digital camera, and facilitating the patient in holding the handheld wound and stoma imaging device in imaging their own wound area or stoma or fistula area on their own body;
displaying a representation on the monitor of an image within a view field of the optical lens;
digitally generating a marker in the image with a processing unit of the handheld wound and stoma imaging device;
inserting the marker in the representation on the monitor of the view field before the image is stored thus assisting the patient in positioning of the digital camera relative to one of a wound site and a stoma site on their own body;
repeating digital image processing of the image within the view field, thus identifying to the patient an area of interest in the one of the wound site and the stoma site on their own body;
updating and controlling a position of the marker in response to movements of the digital camera relative to the area of interest, with the marker aiding the patient in positioning of the digital camera relative to the area of interest within the view field for capturing the one of the wound site and the stoma site on their own body;
configuring the handheld wound and stoma imaging device to allow for simultaneous viewing by the patient of the monitor and the one of the wound site and the stoma site on their own body;
improving image quality by capturing a plurality of successive images using the handheld wound and stoma imaging device independent of input by the patient, performing a qualitative assessment of the plurality of successive images, and selecting one of the plurality of successive images as a selected captured image;
receiving, at the handheld wound and stoma imaging device, an input from the patient and digitally storing the selected captured image in a non-volatile memory of the handheld wound and stoma imaging device; and
assessing at least one of skin discoloration, skin erosion, and tissue overgrowth at the one of the wound site and the stoma site based upon the selected captured image.

2. The method of claim 1, further comprising digitally processing, within the handheld wound and stoma imaging device, the digitally stored selected captured image and providing a measure of a state of healing at the one of the wound site and the stoma site.

3. The method of claim 1, further comprising digitally generating the marker in the image with an applet operating through the handheld wound and stoma imaging device.

4. The method of claim 1, wherein the handheld wound and stoma imaging device comprises a data communication interface for transmitting a digital image to an external device, the method further comprising transmitting the digital image to a healthcare provider.

5. The method of claim 1, wherein the handheld wound and stoma imaging device comprises a data communication interface for transmitting a digital image to an external device, the method further comprising transmitting an image of the skin area surrounding the stoma of the patient to a healthcare provider.

6. The method of claim 1, further comprising digitally processing, within the handheld wound and stoma imaging device, the digitally stored selected captured image and providing at least one value of a measure of a colour change, a measure of a colour, a measure of a contrast, a measure of a surface texture, a measure of a pattern, and a measure of a structure at the one of the wound site and the stoma site.

7. The method of claim 6, further comprising comparing the at least one value from the one of the wound site and the stoma site to a predetermined or pre-stored reference value.

8. The method of claim 1, wherein digitally generating the marker in the image with the processing unit of the handheld wound and stoma imaging device comprises generating a circular frame adapted for aiding the patient in positioning the handheld wound and stoma imaging device relative to the stoma site on their own body, the method further comprising indicating to the patient an object of interest at the stoma site to be positioned within the circular frame prior to capturing the image.

9. The method of claim 1, wherein the handheld wound and stoma imaging device comprises an image capturing controller, the method further comprising:

storing the plurality of successive images in the image capturing controller in a first-in-first-out buffered volatile memory.

10. The method of claim 9, further comprising:

temporarily storing the plurality of successive images in the image capturing controller in the first-in-first-out buffered volatile memory.

11. The method of claim 1, further comprising digitally processing, within the handheld wound and stoma imaging device, an image of a worn wafer and measuring a degree of leakage of the worn wafer.

12. The method of claim 1, further comprising digitally processing, within the handheld wound and stoma imaging device, an image of a worn wafer and measuring a qualitative state of an adhesive of the worn wafer.

* * * * *